(12) United States Patent
Little

(10) Patent No.: US 9,459,195 B2
(45) Date of Patent: Oct. 4, 2016

(54) ESTIMATING POROSITY OR PERMEABILITY IN A REGION OF INTEREST

(71) Applicant: Schlumberger Technology Corporation, Sugar Land, TX (US)

(72) Inventor: Jeffrey D. Little, Bakersfield, CA (US)

(73) Assignee: SCHLUMBERGER TECHNOLOGY CORPORATION, Sugar Land, TX (US)

(*) Notice: Subject to any disclaimer, the term of this patent is extended or adjusted under 35 U.S.C. 154(b) by 251 days.

(21) Appl. No.: 14/322,398

(22) Filed: Jul. 2, 2014

(65) Prior Publication Data

US 2016/0003725 A1    Jan. 7, 2016

(51) Int. Cl.
*G01N 15/08* (2006.01)
*G01V 1/16* (2006.01)

(52) U.S. Cl.
CPC ............ *G01N 15/088* (2013.01); *G01N 15/08* (2013.01); *G01V 1/166* (2013.01)

(58) Field of Classification Search
CPC ..... G01N 15/08; G01N 15/088; G01V 1/166
See application file for complete search history.

(56) References Cited

U.S. PATENT DOCUMENTS

| | | | | |
|---|---|---|---|---|
| 6,142,229 A | * | 11/2000 | Branson, Jr. .......... | E21B 49/008 166/250.15 |
| 8,838,390 B1 | * | 9/2014 | Selman .................... | E21B 44/00 166/264 |
| 2004/0060351 A1 | * | 4/2004 | Gunter ................ | E21B 41/0064 73/152.05 |
| 2006/0042369 A1 | * | 3/2006 | Al-Ruwaili ............ | G01V 1/306 73/152.05 |
| 2010/0030527 A1 | * | 2/2010 | Prasad .................... | E21B 10/00 703/1 |
| 2014/0236487 A1 | * | 8/2014 | Kimman ................ | G01V 1/366 702/18 |

* cited by examiner

*Primary Examiner* — Francis Gray
(74) *Attorney, Agent, or Firm* — Rodney Warfford

(57) ABSTRACT

Disclosed herein are implementations of various technologies for a method for estimating porosity or permeability in a region of interest. The method may receive chemical measurements for the region of interest. The chemical measurements may include an amount of silicon, aluminum, potassium and iron in the region of interest. The method may determine an amount of biogenic silica in the region of interest using the chemical measurements. The method may determine grain density of the region of interest based on the amount of biogenic silica. The method may determine the porosity or permeability in the region of interest based on the grain density.

20 Claims, 7 Drawing Sheets

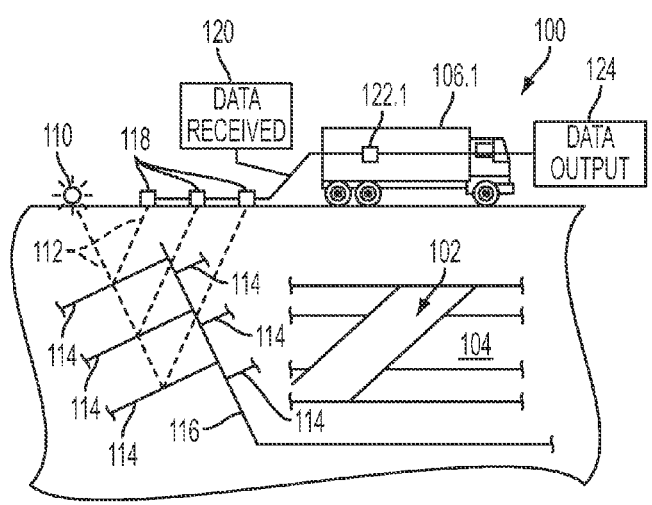
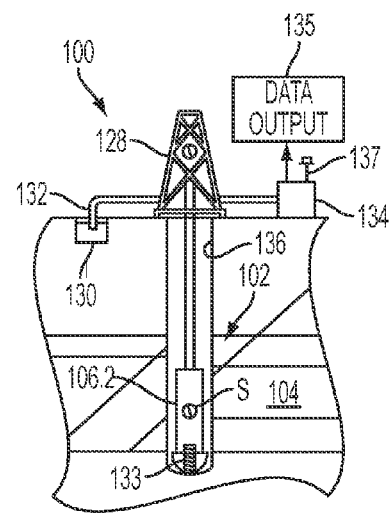
FIG. 1A
FIG. 1B
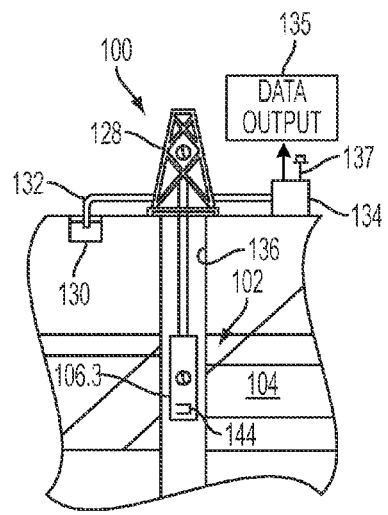
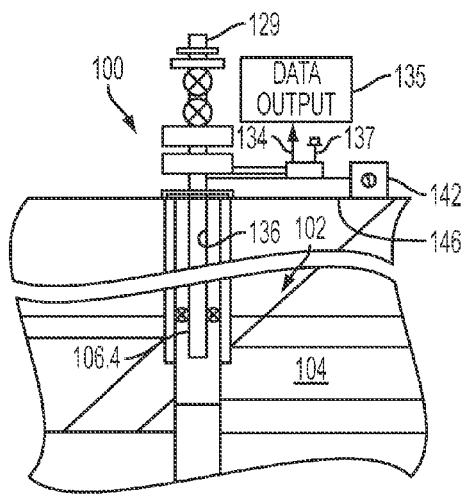
FIG. 1C
FIG. 1D

ESTIMATING POROSITY OR PERMEABILITY IN A REGION OF INTEREST

BACKGROUND

This section is intended to provide background information to facilitate a better understanding of various technologies described herein. As the section's title implies, this is a discussion of related art. That such art is related in no way implies that it is prior art. The related art may or may not be prior art. It should therefore be understood that the statements in this section are to be read in this light, and applicant neither concedes nor acquiesces to the position that any given reference is prior art or analogous prior art.

In order to facilitate the recovery of hydrocarbons from oil and gas wells, the subterranean formations surrounding such wells can be hydraulically fractured. Hydraulic fracturing has become a valuable technique to create cracks in subsurface formations that allow hydrocarbons to move toward the well. Hydraulic fractures may extend away from the wellbore hundreds of feet in two opposing directions according to the natural stresses within the formation. Under certain circumstances, they may form a complex fracture network. Complex fracture networks can include induced hydraulic fractures and natural fractures, which may or may not intersect, along multiple azimuths, in multiple planes and directions, and in multiple regions

SUMMARY

Disclosed herein are implementations of various technologies for a method for estimating porosity or permeability in a region of interest. The method may receive chemical measurements for the region of interest. The chemical measurements may include an amount of silicon, aluminum, potassium and iron in the region of interest. The method may determine an amount of biogenic silica in the region of interest using the chemical measurements. The method may determine grain density of the region of interest based on the amount of biogenic silica. The method may determine the porosity or permeability in the region of interest based on the grain density.

In some implementations, the region of interest may include a predetermined depth in a wellbore. The region of interest may include locations in a shale. The method may determine a first ratio between the amount of silicon in the region of interest and the sum of the amounts of aluminum, potassium, and silicon in the region of interest. The method may determine a second ratio between the amount of iron in the region of interest and a sum of iron and silicon in the region of interest. The method may generate a plot of the first ratio with the second ratio. The plot may include the first ratio plotted on the y-axis of the plot and the second ratio plotted on the x-axis of the plot. The method may determine a threshold line on the plot that represents an approximate minimum amount of biogenic silica in the region of interest. The method may determine a threshold line on the plot that represents an approximate maximum amount of biogenic silica in the region of interest. The plot may include Cartesian coordinates. The method may generate a stimulation plan using the determined porosity or permeability. The stimulation plan may include a fluid viscosity of a fracturing fluid or a rate of injection of a fracturing fluid. The method may determine the presence of hydrocarbon deposits in the region of interest using the determined porosity or determined permeability.

The above referenced summary section is provided to introduce a selection of concepts that are further described below in the detailed description section. The summary is not intended to identify features of the claimed subject matter, nor is it intended to be used to limit the scope of the claimed subject matter. Furthermore, the claimed subject matter is not limited to implementations that solve any or most disadvantages noted in any part of this disclosure.

BRIEF DESCRIPTION OF THE DRAWINGS

Implementations of various technologies will hereafter be described with reference to the accompanying drawings. It should be understood, however, that the accompanying drawings illustrate various implementations described herein and are not meant to limit the scope of various technologies described herein.

FIGS. 1A-1D illustrate schematic views of oilfields in accordance with various implementations described herein.

DETAILED DESCRIPTION

The discussion below is directed to certain specific implementations. It is to be understood that the discussion below is for the purpose of enabling a person with ordinary skill in the art to make and use any subject matter defined now or later by the patent "claims" found in any issued patent herein.

Reference will now be made in detail to various implementations, examples of which are illustrated in the accompanying drawings and figures. In the following detailed description, numerous specific details are set forth in order to provide a thorough understanding of the claimed invention. However, it will be apparent to one of ordinary skill in the art that the claimed invention may be practiced without these specific details. In other instances, well known methods, procedures, components, circuits, and networks have not been described in detail so as not to unnecessarily obscure aspects of the claimed invention.

It will also be understood that, although the terms first, second, etc. may be used herein to describe various elements, these elements should not be limited by these terms. These terms are used to distinguish one element from another. For example, a first object or block could be termed a second object or block, and, similarly, a second object or block could be termed a first object or block, without departing from the scope of the invention. The first object or block, and the second object or block, are both objects or blocks, respectively, but they are not to be considered the same object or block.

The terminology used in the description herein is for the purpose of describing particular implementations and is not intended to limit the claimed invention. As used herein, the singular forms "a", "an" and "the" are intended to include the plural forms as well, unless the context clearly indicates otherwise. It will also be understood that the term "and/or" as used herein refers to and encompasses any possible combinations of one or more of the associated listed items. It will be further understood that the terms "includes," "including," "comprises," and/or "comprising," when used in this specification, specify the presence of stated features, integers, blocks, operations, elements, and/or components, but do not preclude the presence or addition of one or more other features, integers, blocks, operations, elements, components, and/or groups thereof.

As used herein, the term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context.

Figure 5:
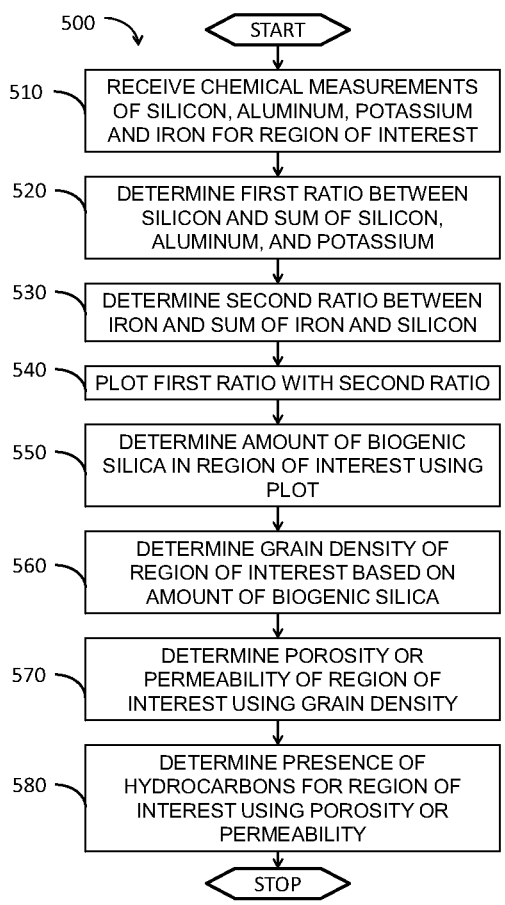
FIG. 5 illustrates a flow diagram of a method for estimating porosity or permeability in accordance with various implementations described herein.

Various techniques described herein are directed to determining the amount of biogenic silica in a region of interest and using the determined biogenic silica in various implementations. FIG. 5 describes a method of estimating porosity or permeability of the region of interest. The section titled OIL OPERATION below generally describes hydrocarbon exploration and production.

Oil Operation

FIGS. 1A-1D illustrate simplified, schematic views of oilfield 100 having subterranean formation 102 containing reservoir 104 therein in accordance with implementations of various technologies and techniques described herein. FIG. 1A illustrates a survey operation being performed by a survey tool, such as seismic truck 106.1, to measure properties of the subterranean formation. The survey operation is a seismic survey operation for producing sound vibrations. In FIG. 1A, one such sound vibration, e.g., sound vibration 112 generated by source 110, reflects off horizons 114 in earth formation 116. A set of sound vibrations is received by sensors, such as geophone-receivers 118, situated on the earth's surface. The data received 120 is provided as input data to a computer 122.1 of a seismic truck 106.1, and responsive to the input data, computer 122.1 generates seismic data output 124. This seismic data output may be stored, transmitted or further processed as desired, for example, by data reduction.

FIG. 1B illustrates a drilling operation being performed by drilling tools 106.2 suspended by rig 128 and advanced into subterranean formations 102 to form wellbore 136. Mud pit 130 is used to draw drilling mud into the drilling tools via flow line 132 for circulating drilling mud down through the drilling tools, then up wellbore 136 and back to the surface. The drilling mud is filtered and returned to the mud pit. A circulating system may be used for storing, controlling, or filtering the flowing drilling mud. The drilling tools are advanced into subterranean formations 102 to reach reservoir 104. Each well may target one or more reservoirs. The drilling tools are adapted for measuring downhole properties using logging while drilling tools. The logging while drilling tools may also be adapted for taking core sample 133 as shown.

Computer facilities may be positioned at various locations about the oilfield 100 (e.g., the surface unit 134) and/or at remote locations. Surface unit 134 may be used to communicate with the drilling tools and/or offsite operations, as well as with other surface or downhole sensors. Surface unit 134 is capable of communicating with the drilling tools to send commands to the drilling tools, and to receive data therefrom. Surface unit 134 may also collect data generated during the drilling operation and produce data output 135, which may then be stored or transmitted.

Sensors (S), such as gauges, may be positioned about oilfield 100 to collect data relating to various oilfield operations as described previously. As shown, sensor (S) is positioned in one or more locations in the drilling tools and/or at rig 128 to measure drilling parameters, such as weight on bit, torque on bit, pressures, temperatures, flow rates, compositions, rotary speed, and/or other parameters of the field operation. Sensors (S) may also be positioned in one or more locations in the circulating system.

Drilling tools 106.2 may include a bottom hole assembly (BHA) (not shown), generally referenced, near the drill bit (e.g., within several drill collar lengths from the drill bit). The bottom hole assembly includes capabilities for measuring, processing, and storing information, as well as communicating with surface unit 134. The bottom hole assembly further includes drill collars for performing various other measurement functions.

The bottom hole assembly may include a communication subassembly that communicates with surface unit 134. The communication subassembly is adapted to send signals to and receive signals from the surface using a communications channel such as mud pulse telemetry, electro-magnetic telemetry, or wired drill pipe communications. The communication subassembly may include, for example, a transmitter that generates a signal, such as an acoustic or electro-magnetic signal, which is representative of the measured drilling parameters. It will be appreciated by one of skill in the art that a variety of telemetry systems may be employed, such as wired drill pipe, electromagnetic or other known telemetry systems.

The wellbore may be drilled according to a drilling plan that is established prior to drilling. The drilling plan may set forth equipment, pressures, trajectories and/or other parameters that define the drilling process for the wellsite. The drilling operation may then be performed according to the drilling plan. However, as information is gathered, the drilling operation may need to deviate from the drilling plan. Additionally, as drilling or other operations are performed, the subsurface conditions may change. The earth model may also need adjustment as new information is collected.

The data gathered by sensors (S) may be collected by surface unit 134 and/or other data collection sources for analysis or other processing. The data collected by sensors (S) may be used alone or in combination with other data. The data may be collected in one or more databases and/or transmitted on or offsite. The data may be historical data, real time data, or combinations thereof. The real time data may be used in real time, or stored for later use. The data may also be combined with historical data or other inputs for further analysis. The data may be stored in separate databases, or combined into a single database.

Surface unit 134 may include transceiver 137 to allow communications between surface unit 134 and various portions of the oilfield 100 or other locations. Surface unit 134 may also be provided with or functionally connected to one or more controllers (not shown) for actuating mechanisms at oilfield 100. Surface unit 134 may then send command signals to oilfield 100 in response to data received. Surface unit 134 may receive commands via transceiver 137 or may itself execute commands to the controller. A processor may be provided to analyze the data (locally or remotely), make the decisions and/or actuate the controller. In this manner, oilfield 100 may be selectively adjusted based on the data collected. This technique may be used to optimize portions of the field operation, such as controlling drilling, weight on bit, pump rates, or other parameters. These adjustments may be made automatically based on computer protocol, and/or manually by an operator. In some cases, well plans may be adjusted to select optimum operating conditions, or to avoid problems.

FIG. 1C illustrates a wireline operation being performed by wireline tool 106.3 suspended by rig 128 and into wellbore 136 of FIG. 1B. Wireline tool 106.3 is adapted for deployment into wellbore 136 for generating well logs, performing downhole tests and/or collecting samples. Wireline tool 106.3 may be used to provide another method and apparatus for performing a seismic survey operation. Wireline tool 106.3 may, for example, have an explosive, radioactive, electrical, or acoustic energy source 144 that sends and/or receives electrical signals to surrounding subterranean formations 102 and fluids therein.

Wireline tool 106.3 may be operatively connected to, for example, geophones 118 and a computer 122.1 of a seismic truck 106.1 of FIG. 1A. Wireline tool 106.3 may also provide data to surface unit 134. Surface unit 134 may collect data generated during the wireline operation and may produce data output 135 that may be stored or transmitted. Wireline tool 106.3 may be positioned at various depths in the wellbore 136 to provide a survey or other information relating to the subterranean formation 102.

Sensors (S), such as gauges, may be positioned about oilfield 100 to collect data relating to various field operations as described previously. As shown, sensor S is positioned in wireline tool 106.3 to measure downhole parameters which relate to, for example porosity, permeability, fluid composition and/or other parameters of the field operation.

FIG. 1D illustrates a production operation being performed by production tool 106.4 deployed from a production unit or Christmas tree 129 and into completed wellbore 136 for drawing fluid from the downhole reservoirs into surface facilities 142. The fluid flows from reservoir 104 through perforations in the casing (not shown) and into production tool 106.4 in wellbore 136 and to surface facilities 142 via gathering network 146.

Sensors (S), such as gauges, may be positioned about oilfield 100 to collect data relating to various field operations as described previously. As shown, the sensor (S) may be positioned in production tool 106.4 or associated equipment, such as Christmas tree 129, gathering network 146, surface facility 142, and/or the production facility, to measure fluid parameters, such as fluid composition, flow rates, pressures, temperatures, and/or other parameters of the production operation.

Production may also include injection wells for added recovery. One or more gathering facilities may be operatively connected to one or more of the wellsites for selectively collecting downhole fluids from the wellsite(s).

While FIGS. 1B-1D illustrate tools used to measure properties of an oilfield, it will be appreciated that the tools may be used in connection with non-oilfield operations, such as gas fields, mines, aquifers, storage or other subterranean facilities. Also, while certain data acquisition tools are depicted, it will be appreciated that various measurement tools capable of sensing parameters, such as seismic two-way travel time, density, resistivity, production rate, etc., of the subterranean formation and/or its geological formations may be used. Various sensors (S) may be located at various positions along the wellbore and/or the monitoring tools to collect and/or monitor the desired data. Other sources of data may also be provided from offsite locations.

The field configurations of FIGS. 1A-1D are intended to provide a brief description of an example of a field usable with oilfield application frameworks. Part of, or the complete, oilfield 100 may be on land, water, and/or sea. Also, while a single field measured at a single location is depicted, oilfield applications may be utilized with any combination of one or more oilfields, one or more processing facilities and one or more wellsites.

Figure 2:
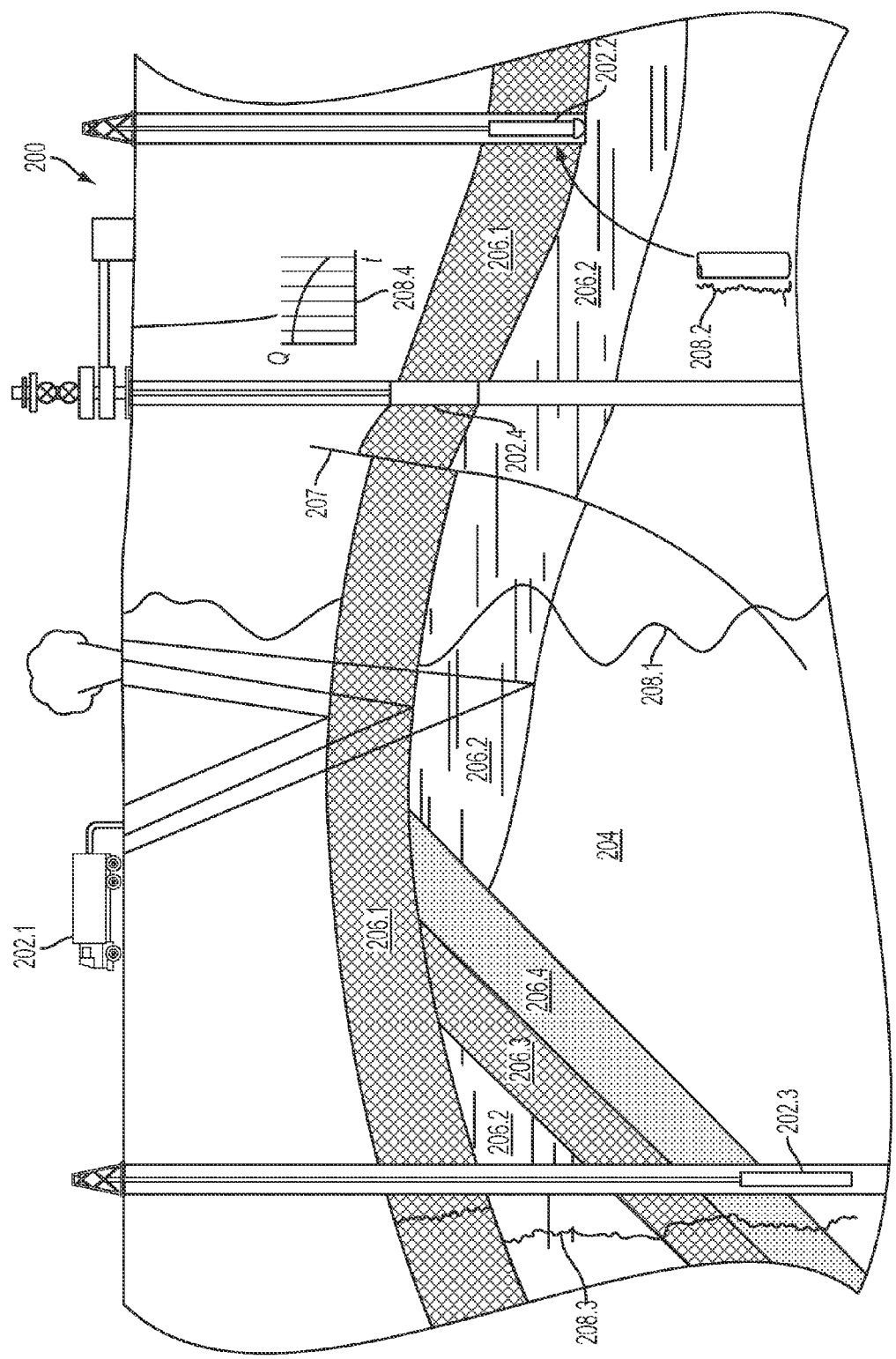
FIG. 2 illustrates a schematic view of an oilfield in accordance with various implementations described herein.

FIG. 2 illustrates a schematic view, partially in cross section of oilfield 200 having data acquisition tools 202.1, 202.2, 202.3 and 202.4 positioned at various locations along oilfield 200 for collecting data of subterranean formation 204 in accordance with implementations of various technologies and techniques described herein. Data acquisition tools 202.1-202.4 may be the same as data acquisition tools 106.1-106.4 of FIGS. 1A-1D, respectively, or others not depicted. As shown, data acquisition tools 202.1-202.4 generate data plots or measurements 208.1-208.4, respectively. These data plots are depicted along oilfield 200 to demonstrate the data generated by the various operations.

Data plots 208.1-208.3 are examples of static data plots that may be generated by data acquisition tools 202.1-202.3, respectively; however, it should be understood that data plots 208.1-208.3 may also be data plots that are updated in real time. These measurements may be analyzed to better define the properties of the formation(s) and/or determine the accuracy of the measurements and/or for checking for errors. The plots of each of the respective measurements may be aligned and scaled for comparison and verification of the properties.

Static data plot 208.1 is a seismic two-way response over a period of time. Static plot 208.2 is core sample data measured from a core sample of the formation 204. The core sample may be used to provide data, such as a graph of the density, porosity, permeability, or some other physical property of the core sample over the length of the core. Tests for density and viscosity may be performed on the fluids in the core at varying pressures and temperatures. Static data plot 208.3 is a logging trace that provides a resistivity or other measurement of the formation at various depths.

A production decline curve or graph 208.4 is a dynamic data plot of the fluid flow rate over time. The production decline curve provides the production rate as a function of time. As the fluid flows through the wellbore, measurements are taken of fluid properties, such as flow rates, pressures, composition, etc.

Other data may also be collected, such as historical data, user inputs, economic information, and/or other measurement data and other parameters of interest. As described below, the static and dynamic measurements may be analyzed and used to generate models of the subterranean formation to determine characteristics thereof. Similar measurements may also be used to measure changes in formation aspects over time.

The subterranean structure 204 has a plurality of geological formations 206.1-206.4. As shown, this structure has several formations or layers, including a shale layer 206.1, a carbonate layer 206.2, a shale layer 206.3 and a sand layer 206.4. A fault 207 extends through the shale layer 206.1 and the carbonate layer 206.2. The static data acquisition tools are adapted to take measurements and detect characteristics of the formations.

While a specific subterranean formation with specific geological structures is depicted, it will be appreciated that oilfield 200 may contain a variety of geological structures and/or formations, sometimes having extreme complexity. In some locations, typically below the water line, fluid may occupy pore spaces of the formations. Each of the measurement devices may be used to measure properties of the formations and/or its geological features. While each acquisition tool is shown as being in specific locations in oilfield 200, it will be appreciated that one or more types of measurement may be taken at one or more locations across one or more fields or other locations for comparison and/or analysis.

The data collected from various sources, such as the data acquisition tools of FIG. 2, may then be processed and/or evaluated. Typically, seismic data displayed in static data plot 208.1 from data acquisition tool 202.1 is used by a geophysicist to determine characteristics of the subterranean formations and features. The core data shown in static plot 208.2 and/or log data from well log 208.3 are typically used by a geologist to determine various characteristics of the subterranean formation. The production data from graph 208.4 is typically used by the reservoir engineer to determine fluid flow reservoir characteristics. The data analyzed by the geologist, geophysicist and the reservoir engineer may be analyzed using modeling techniques.

Figure 3:
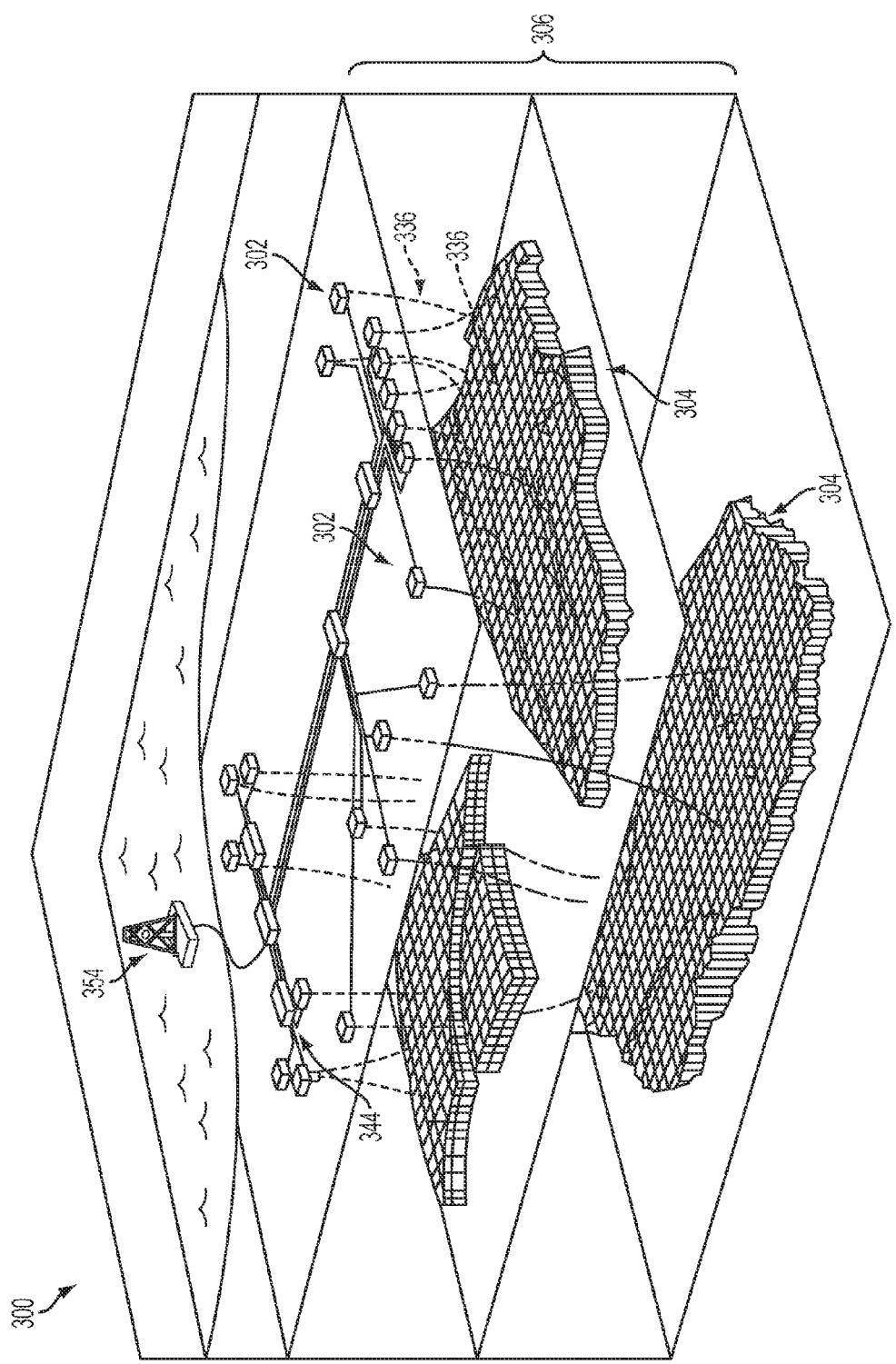
FIG. 3 illustrates an oilfield in accordance with various implementations described herein.

FIG. 3 illustrates an oilfield 300 for performing production operations in accordance with implementations of various technologies and techniques described herein. As shown, the oilfield has a plurality of wellsites 302 operatively connected to central processing facility 354. The oilfield configuration of FIG. 3 is not intended to limit the scope of the oilfield application system. Part, or the entirety, of the oilfield may be on land and/or sea. Also, while a single oilfield with a single processing facility and a plurality of wellsites is depicted, any combination of one or more oilfields, one or more processing facilities and one or more wellsites may be present.

Each wellsite 302 has equipment that forms wellbore 336 into the earth. The wellbores extend through subterranean formations 306 including reservoirs 304. These reservoirs 304 contain fluids, such as hydrocarbons. The wellsites draw fluid from the reservoirs and pass them to the processing facilities via surface networks 344. The surface networks 344 have tubing and control mechanisms for controlling the flow of fluids from the wellsite to processing facility 354.

Figure 4:
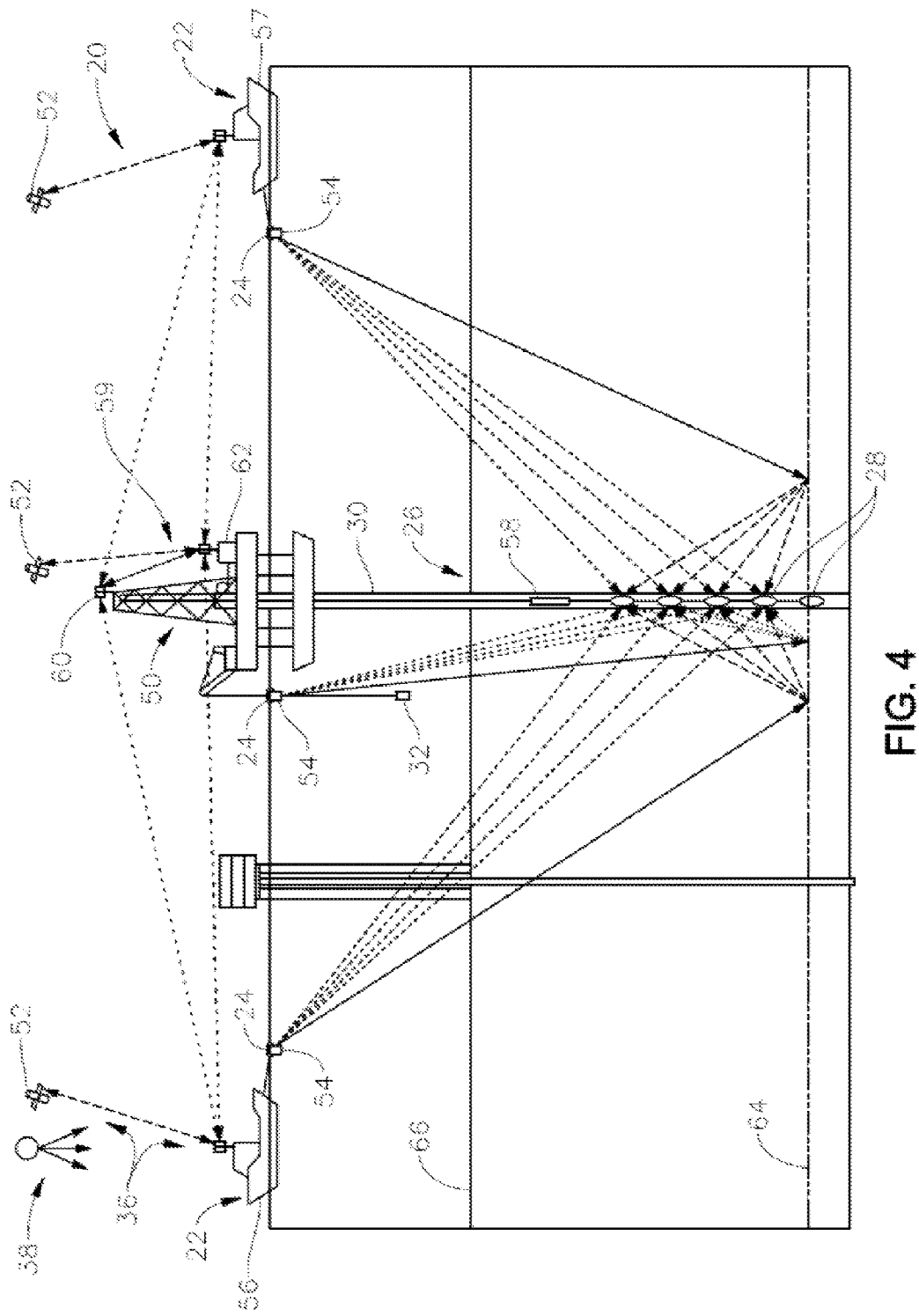
FIG. 4 illustrates a seismic system in accordance with various implementations described herein.

Attention is now directed to FIG. 4 that depicts an embodiment of seismic system 20 in which a plurality of tow vessels 22 is employed to enable seismic profiling, e.g. three-dimensional vertical seismic profiling or rig/offset vertical seismic profiling. In FIG. 4, a marine system is illustrated as including a rig 50, a plurality of vessels 22, and one or more acoustic receivers 28. Although a marine system is illustrated, other embodiments of the disclosure may not be limited to this example. A person of ordinary skill in the art will recognize that teachings of the disclosure may be used in land or offshore systems. However, offshore systems are described herein to simplify the disclosure and to facilitate explanation.

Although two vessels 22 are illustrated in FIG. 4, a single vessel 22 with multiple source arrays 24 or multiple vessels 22 each with single or multiple sources 24 may be used. In some applications, at least one source/source array 24 may be located on the rig 50 as represented by the rig source in FIG. 4. As the vessels 22 travel on predetermined or systematic paths, their locations may be recorded through the use of navigation system 36. In some cases, the navigation system 36 utilizes a global positioning system (GPS) 38 to record the position, speed, direction, and other parameters of the tow vessels 22.

As illustrated, the global positioning system 38 may utilize or work in cooperation with satellites 52 which operate on a suitable communication protocol, e.g. VSAT communications. The VSAT communications may be used, among other things, to supplement VHF and UHF communications. The GPS information can be independent of the VSAT communications and may be input to processing system or other suitable processors to predict the future movement and position of the vessels 22 based on real-time information. In addition to predicting future movements, the processing system also can be utilized to provide directions and coordinates as well as to determine initial shot times, as described above. Control system 34 effectively utilizes processing system in cooperation with source controller and synchronization unit to synchronize the sources 24 with the downhole data acquisition system 26.

As illustrated, the one or more vessels 22 each tow one or more acoustic sources/source arrays 24. The source arrays 24 include one or more seismic signal generators 54, e.g. air guns, configured to create a seismic/sonic disturbance. In the embodiment illustrated, the tow vessels 22 comprise a master source vessel 56 (Vessel A) and a slave source vessel 57 (Vessel B). However, other numbers and arrangements of tow vessels 22 may be employed to accommodate the parameters of a given seismic profiling application. For example, one source 24 may be mounted at rig 50 (see FIG. 4) or at another suitable location, and both vessels 22 may serve as slave vessels with respect to the rig source 24 or with respect to a source at another location.

However, a variety of source arrangements and implementations may be provided as desired for a given application. When utilizing dithered timing between the sources, for example, the master and slave locations of the sources can be adjusted according to the parameters of the specific seismic profiling application. In some applications, one of the source vessels 22 (e.g. source vessel A in FIG. 4) may serve as the master source vessel while the other source vessel 22 serves as the slave source vessel with dithered firing. However, an alternate source vessel 22 (e.g. source vessel B in FIG. 4) may serve as the master source vessel while the other source vessel 22 serves as the slave source vessel with dithered firing.

Similarly, the rig source 24 may serve as the master source while one of the source vessels 22 (e.g. vessel A) serves as the slave source vessel with dithered firing. The rig source 24 also may serve as the master source while the other source vessel 22 (e.g. vessel B) serves as the slave source vessel with dithered firing. In some applications, the rig source 24 may serve as the master source while both of the source vessels 22 serve as slave source vessels each with dithered firings. These and other arrangements may be used in achieving the desired synchronization of sources 24 with the downhole acquisition system 26.

The acoustic receivers 28 of data acquisition system 26 may be deployed in borehole 30 via a variety of delivery systems, such as wireline delivery systems, slickline delivery systems, and other suitable delivery systems. Although a single acoustic receiver 28 could be used in the borehole 30, the illustrated embodiment comprises a plurality of receivers 28 that may be located in a variety of positions and orientations. The acoustic receivers 28 may be configured for sonic and/or seismic reception. Additionally, the acoustic receivers 28 may be communicatively coupled with processing equipment 58 located downhole. By way of example, processing equipment 58 may comprise a telemetry system for transmitting data from acoustic receivers 28 to additional processing equipment 59 located at the surface, e.g. on the rig 50 and/or vessels 22.

Depending on the specifics of a given data communication system, examples of surface processing equipment 59 may comprise a radio repeater 60, an acquisition and logging unit 62, and a variety of other and/or additional signal transfer components and signal processing components. The radio repeater 60 along with other components of processing equipment 59 may be used to communicate signals, e.g. UHF and/or VHF signals, between vessels 22 and rig 50 and to enable further communication with downhole data acquisition system 26.

It should be noted the UHF and VHF signals can be used to supplement each other. In general, the UHF band supports a higher data rate throughput but can be susceptible to obstructions and has less range. The VHF band is less susceptible to obstructions and has increased radio range but its data rate throughput is lower. In FIG. 4, for example, the VHF communications are illustrated as "punching through" an obstruction in the form of a production platform.

In some applications, the acoustic receivers 28 are coupled to surface processing equipment 59 via a hardwired connection. In other embodiments, wireless or optical connections may be employed. In still other embodiments, combinations of coupling techniques may be employed to relay information received downhole via the acoustic receivers 28 to an operator and/or control system, e.g. control system, located at least in part at the surface.

In addition to providing raw or processed data uphole to the surface, the coupling system, e.g. downhole processing equipment 58 and surface processing equipment 59, may be designed to transmit data or instructions downhole to the acoustic receivers 28. For example, the surface processing equipment 59 may comprise synchronization unit which coordinates the firing of sources 24, e.g. dithered (delayed) source arrays, with the acoustic receivers 28 located in borehole 30. According to one embodiment, the synchronization unit uses coordinated universal time to ensure accurate timing. In some cases, the coordinated universal time system is employed in cooperation with global positioning system 38 to obtain UTC data from the GPS receivers of GPS system 38.

FIG. 4 illustrates one example of a system for performing seismic profiling that can employ simultaneous or near-simultaneous acquisition of seismic data. By way of example, the seismic profiling may comprise three-dimensional vertical seismic profiling but other applications may utilize rig/offset vertical seismic profiling or seismic profiling employing walkaway lines. An offset source can be provided by a source 24 located on rig 50, on a stationary vessel 22, and/or on another stationary vessel or structure.

As an example, the overall seismic system 20 may employ various arrangements of sources 24 on vessels 22 and/or rig 50 with each location having at least one source/source array 24 to generate acoustic source signals. The acoustic receivers 28 of downhole acquisition system 26 are configured to receive the source signals, at least some of which are reflected off a reflection boundary 64 located beneath a sea bottom 66. The acoustic receivers 28 generate data streams that are relayed uphole to a suitable processing system, e.g. processing system, via downhole telemetry/processing equipment 58.

While the acoustic receivers 28 generate data streams, the navigation system 36 determines a real-time speed, position, and direction of each vessel 22 and also estimates initial shot times accomplished via signal generators 54 of the appropriate source arrays 24. The source controller may be part of surface processing equipment 59 (located on rig 50, on vessels 22, or at other suitable locations) and is designed to control firing of the acoustic source signals so that the timing of an additional shot time (e.g. a shot time via slave vessel 57) is based on the initial shot time (e.g. a shot time via master vessel 56) plus a dither value.

The synchronization unit of, for example, surface processing equipment 59, coordinates the firing of dithered acoustic signals with recording of acoustic signals by the downhole acquisition system 26. Processor system is configured to separate a data stream of the initial shot and a data stream of the additional shot via the coherency filter. As discussed above, however, other embodiments may employ pure simultaneous acquisition and/or may not perform separation of the data streams. In such cases, the dither is effectively zero.

After an initial shot time at T=0 (T0) is determined, subsequent firings of acoustic source arrays 24 may be offset by a dither. The dithers can be positive or negative and sometimes are created as pre-defined random delays. Use of dithers facilitates the separation of simultaneous or near-simultaneous data sets to simplify the data processing. The ability to have the acoustic source arrays 24 fire in simultaneous or near-simultaneous patterns reduces the overall amount of time used for three-dimensional vertical seismic profiling source acquisition. This, in turn, reduces rig time. As a result, the overall cost of the seismic operation is reduced, rendering the data intensive process much more accessible.

If the acoustic source arrays used in the seismic data acquisition are widely separated, the difference in move-outs across the acoustic receiver array of the wave fields generated by the acoustic sources 24 can be sufficient to obtain a clean data image via processing the data without further special considerations. However, even when the acoustic sources 24 are substantially co-located in time, data acquired by any of the methods involving dithering of the firing times of the individual sources 24 described herein can be processed to a formation image leaving hardly any artifacts in the final image. This is accomplished by taking advantage of the incoherence of the data generated by one acoustic source 24 when seen in the reference time of the other acoustic source 24.

Reservoir Data Processing

Stimulation operations for conventional and unconventional reservoirs may be performed based on knowledge of reservoirs. For instance, a shale reservoir may be an example of an unconventional reservoir. Shale reservoirs may have various types of lithology and include formations directed to calcareous, dolostone, or biogenic silica. In a biogenic silica shale, two types of silicon dioxide SiO2 may be present, Silica dioxide ($SiO_2$) and hydrated forms of Silica Dioxide ($SiO_2*nH_2O$), e.g., detrital forms of silica and biogenic silica, respectively. Detrital silica may describe silica that is rich in quartz sandstones and other detrital sediments. Biogenic silica (bSi) may include a chalk-like fine-grained siliceous sedimentary rock that originated through biogenic processes. As such, biogenic silica may refer to wide variety of different compounds such as Diatomite, Diatomaceous Claystone, Diatomaceous Clay, Diatomaceous Shale, Porcellanite, Porcelaneous Shale, Porcelaneous Chert, Chert, Opal-A (Amorphous Silica), and Opal CT (Cristobalite, Tridymite Silica).

Reservoir characterizations may include determining the quantities of biogenic silica and detrital silica throughout a particular reservoir. Evaluating the geochemical composition of basin deposits in the particular reservoir may be performed by separating the biogenic silica components from the detrital silica in the particular reservoir. Misidentifying rock in a particular reservoir as biogenic silica or detrital silica may result in an overestimation of hydrocarbons. As such, an accurate reservoir characterization may be used in well planning, identifying optimal target zones for perforation and staging, designing of multiple wells (e.g., spacing and orientation), and geomechanical models.

FIG. 5 illustrates a flow diagram of a method 500 for estimating porosity or permeability in accordance with various implementations described herein. It should be understood that while the operational flow diagram indicates a particular order of execution of the operations, in other implementations, the operations might be executed in a different order. Further, in some implementations, additional operations or blocks may be added to the method. Likewise, some operations or blocks may be omitted.

At block 510, a plurality of chemical measurements may be received for a region of interest. The received chemical measurements may be a dataset that includes one or more estimates regarding the amounts of silicon, aluminum, potassium, and iron in the region of interest. The region of interest may be one or more predetermined depths inside a wellbore or a borehole. In one implementation, the region of interest for the chemical measurements may be directed to different locations in a potential reservoir, such as a biogenic shale or another type of shale.

Further, the chemical measurements may include various weights of elements that are present in a rock specimen in the region of interest. Elemental weights may describe the fraction or percentage of a particular rock that corresponds to a particular element, such as silicon, aluminum, potassium or iron. Potassium-feldspar, for example, may have elemental weights directed to potassium, silicon, aluminum and oxygen. The elemental weights of a rock specimen may be determined using various types of spectroscopy, such as pulsed neutron spectroscopy. Furthermore, the chemical measurements may be recorded in a well log that notes the various elemental weights of rock at various depths inside a wellbore.

At block 520, a first ratio may be determined between the amount of silicon and the sum of silicon, aluminum and potassium for the region of interest. For instance, the first ratio may be a function that may be expressed by the following equation:

$$f_1(Si, K, Al) = \frac{Si}{K + Al + Si} \qquad \text{Equation 1}$$

where Si represents the amount of silicon as a percentage of an analyzed rock, K represents the amount of potassium as a percentage of the analyzed rock, and Al represents the amount of aluminum as a percentage of the analyzed rock. The values of Si, K, Al for the analyzed rock may be obtained from the chemical measurements received at block 510, and where the analyzed rock may be a particular rock in the region of interest.

At block 530, a second ratio may be determined between the amounts of iron and the sum of silicon and iron for the region of interest. For instance, the second ratio may be a function that may be expressed by the following equation:

$$f_2(Si, Fe) = \frac{Fe}{Fe + Si} \qquad \text{Equation 2}$$

where Si represents the amount of silicon as a percentage of the analyzed rock, and Fe represents the amount of iron as a percentage of the analyzed rock. The values of Si and Fe may be obtained from the chemical measurements received at block 510.

Figure 6:
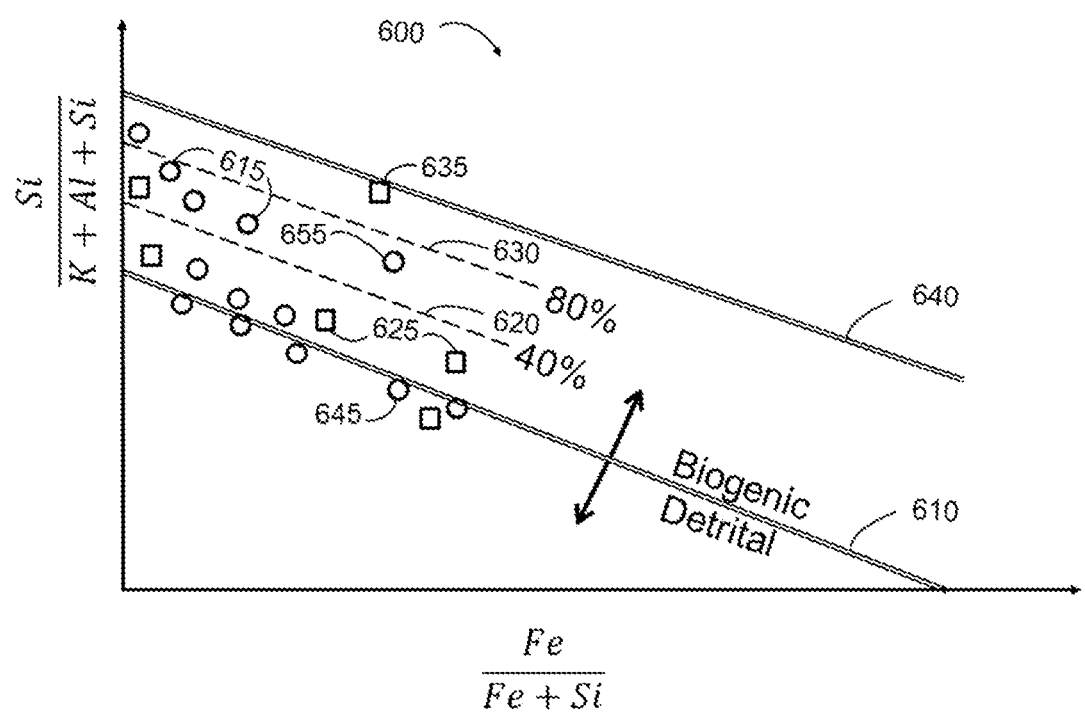
FIG. 6 illustrates an example of a generated plot in accordance with various implementations described herein.

At block 540, the first ratio may be plotted with the second ratio, as shown in FIG. 6 that illustrates an example of a generated plot 600. The generated plot 600 may describe various chemical measurements taken from a first wellbore and a second wellbore for a region of interest. A circle or square on the generated plot 600 may represent a data point for a predetermined location inside a wellbore where chemical measurements were acquired. Based on the chemical measurements for the data points, the respective circles or squares may be plotted using the first ratio from block 520 and the second ratio from block 530. Using Cartesian coordinates, the first ratio corresponds to the y-axis of the generated plot 600, while the second ratio corresponds to the x-axis. Data points 615 acquired from the first wellbore may be circles, while data points 625 acquired from the second wellbore may be squares.

Keeping with FIG. 6, a minimum threshold line 610 on the generated plot 600 may represent the approximate minimum amount of biogenic silica found in analyzed rock. As such, data points near or below the minimum threshold line 610 may describe analyzed rock that primarily contains detrital silica. Data points that are found farther above the minimum threshold line 610 may illustrate analyzed rock with increasing amounts of biogenic silica. Threshold lines 620 and 630 may represent levels of biogenic silica where the percentage of biogenic silica in the analyzed rock is at 40% or 80%, respectively.

Furthermore, a maximum threshold line 640 may represent an approximate maximum amount of biogenic silica found in analyzed rock. For instance, the data point 635 near the maximum threshold line 640 may correspond to analyzed rock with approximately 100% biogenic silica content. The threshold lines 610, 620, 630 and 640 may be determined using rock specimens from the region of interest or estimated based on the chemical measurements from block 510.

Returning to FIG. 5, at block 550, the amount of biogenic silica in the region of interest may be determined using the generated plot 600. For example, the determined amount of biogenic silica may be an absolute number (e.g., 35% of rock at a respective location) or a range of values (e.g., between 40% and 60% of the rock may be biogenic silica at the respective location). Based on the corresponding location of data points in the generated plot 600, areas in the region of interest that are high or low in biogenic silica may be mapped to produce a rock matrix for the region of interest.

In another implementation, the distance of the respective data point on the generated plot 600 from the maximum threshold line 640 or the minimum threshold line 610 may provide an estimate of biogenic silica at that respective data point's location. For instance, data point 655 may have between 40% and 80% biogenic silica in the corresponding rock for that location. Data point 635 that is located just below the maximum threshold line 640 may have biogenic silica content that is close to 100%. Data point 645 that is located below the minimum threshold line 610 may be completely detrital silica and have no biogenic silica content present. As such, FIG. 6 may be used to determine the absence or presence of biogenic silica in various rock formations for the region of interest.

In other implementations of method 500, the amount of biogenic silica may be determined without using a generated plot. For instance, computed values for the first ratio from block 520, the second ratio from block 530, the minimum threshold line 610 and/or the maximum threshold line 640 may be parameterized into a closed-form expression or equation.

At block 560, the grain density of the region of interest may be determined using the amount of biogenic silica determined at block 550. Biogenic silica may contribute to a low grain density to various rock formations. Opal-A, which is one type of biogenic silica, may have a grain density of 2.08. In comparison, quartz sandstone that is composed primarily of detrital silica may have a grain density of 2.65. In characterizing a reservoir, estimating the amount of biogenic silica in the region of interest may provide for the separation of hydrated and/or microporous biogenic silica from other forms of silica.

At block 570, the porosity or permeability of the region of interest may be determined using the grain density determined at block 560. Rock porosity is the percentage of void space in rock, while permeability is a measure of the ability of a porous material to allow fluid to pass through the porous material. To determine rock porosity $\phi$ in the region of interest, the grain density from block 560 may be used in the following equation:

$$\phi = \frac{\rho_L - \rho_g}{\rho_f - \rho_g} \qquad \text{Equation 3}$$

where $\rho_g$ is the grain density of a physical medium, $\rho_L$ is the density of the physical medium, which may be measured from a density or gravimetric log, and $\rho_f$ is the fluid density of the physical medium.

Permeability for the region of interest may be determined based on the rock porosity and the volume of biogenic silica and other materials (e.g., clay, calcite, etc.) in the region of interest.

At block 580, the porosity or the permeability from block 570 may be used to determine the presence of hydrocarbons for region of interest. For more information regarding hydrocarbon exploration or production, see the section titled OIL OPERATION above.

In one implementation, a stimulation plan may be designed or generated for the region of interest based on the determined porosity or permeability from block 570. The stimulation plan may describe oilfield or gas operations that may be performed in advance of performing such operations at a wellsite. The stimulation plan may be used to define, for example, equipment and operating parameters for performing the oilfield or gas operations. Some such operating parameters may include, for example, perforating locations, injection rate of a fracturing fluid, fluid viscosity of a fracturing fluid, operating pressures, stimulation fluids, and other parameters used in stimulation.

In some implementations, a method for estimating porosity or permeability in a region of interest is provided. The method may receive chemical measurements for the region of interest. The chemical measurements may include an amount of silicon, aluminum, potassium and iron in the region of interest. The method may determine an amount of biogenic silica in the region of interest using the chemical measurements. The method may determine grain density of the region of interest based on the amount of biogenic silica. The method may determine the porosity or permeability of the region of interest based on the determined grain density.

In some implementations, the region of interest may include a predetermined depth in a wellbore. The region of interest may include locations in a shale. The method may determine a first ratio between the amount of silicon in the region of interest and the sum of the amounts of aluminum, potassium, and silicon in the region of interest. The method may determine a second ratio between the amount of iron in the region of interest and a sum of iron and silicon in the region of interest. The method may generate a plot of the first ratio with the second ratio. The plot may include the first ratio plotted on the y-axis of the plot and the second ratio plotted on the x-axis of the plot. The method may determine a threshold line on the plot that represents an approximate minimum amount of biogenic silica in the region of interest. The method may determine a threshold line on the plot that represents an approximate maximum amount of biogenic silica in the region of interest. The plot may include Cartesian coordinates. The method may generate a stimulation plan using the determined porosity or permeability. The stimulation plan may include a fluid viscosity of a fracturing fluid or a rate of injection of a fracturing fluid. The method may determine the presence of hydrocarbon deposits in the region of interest using the determined porosity or determined permeability.

In some implementations, an information processing apparatus for use in a computing system is provided, and includes means for receiving chemical measurements for a region of interest. The chemical measurements may include an amount of silicon, aluminum, potassium and iron in the region of interest. The information processing apparatus may also have means for determining an amount of biogenic silica in the region of interest using the chemical measurements. The information processing apparatus may also have means for determining grain density of the region of interest based on the amount of biogenic silica. The information processing apparatus may also have means for determining porosity or permeability of the region of interest based on the determined grain density.

In some implementations, a computing system is provided that includes at least one processor, at least one memory, and one or more programs stored in the at least one memory, wherein the programs include instructions, which when executed by the at least one processor cause the computing system to receive chemical measurements for a region of interest. The chemical measurements may include an amount of silicon, aluminum, potassium and iron in the region of interest. The programs may further include instructions to cause the computing system to determine an amount of biogenic silica in the region of interest using the chemical measurements. The programs may further include instructions to cause the computing system to determine grain density of the region of interest based on the amount of biogenic silica. The programs may further include instructions to cause the computing system to determine porosity or permeability of the region of interest based on the determined grain density.

In some implementations, a computer readable storage medium is provided, which has stored therein one or more programs, the one or more programs including instructions, which when executed by a processor, cause the processor to receive chemical measurements for a region of interest. The chemical measurements may include an amount of silicon, aluminum, potassium and iron in the region of interest. The programs may further include instructions, which cause the processor to determine an amount of biogenic silica using the chemical measurements. The programs may further include instructions, which cause the processor to determine grain density of the region of interest based on the amount of biogenic silica. The programs may further include instructions, which cause the processor to determine porosity or permeability of the region of interest based on the determined grain density.

Computing System

Implementations of various technologies described herein may be operational with numerous general purpose or special purpose computing system environments or configurations. Examples of well known computing systems, environments, and/or configurations that may be suitable for use with the various technologies described herein include, but are not limited to, personal computers, server computers, hand-held or laptop devices, multiprocessor systems, microprocessor-based systems, set top boxes, programmable consumer electronics, network PCs, minicomputers, mainframe computers, smartphones, smartwatches, personal wearable computing systems networked with other computing systems, tablet computers, and distributed computing environments that include any of the above systems or devices, and the like.

The various technologies described herein may be implemented in the general context of computer-executable instructions, such as program modules, being executed by a computer. Generally, program modules include routines, programs, objects, components, data structures, etc. that performs particular tasks or implement particular abstract data types. While program modules may execute on a single computing system, it should be appreciated that, in some implementations, program modules may be implemented on separate computing systems or devices adapted to communicate with one another. A program module may also be some combination of hardware and software where particular tasks performed by the program module may be done either through hardware, software, or both.

The various technologies described herein may also be implemented in distributed computing environments where tasks are performed by remote processing devices that are linked through a communications network, e.g., by hardwired links, wireless links, or combinations thereof. The distributed computing environments may span multiple continents and multiple vessels, ships or boats. In a distributed computing environment, program modules may be located in both local and remote computer storage media including memory storage devices.

Figure 7:
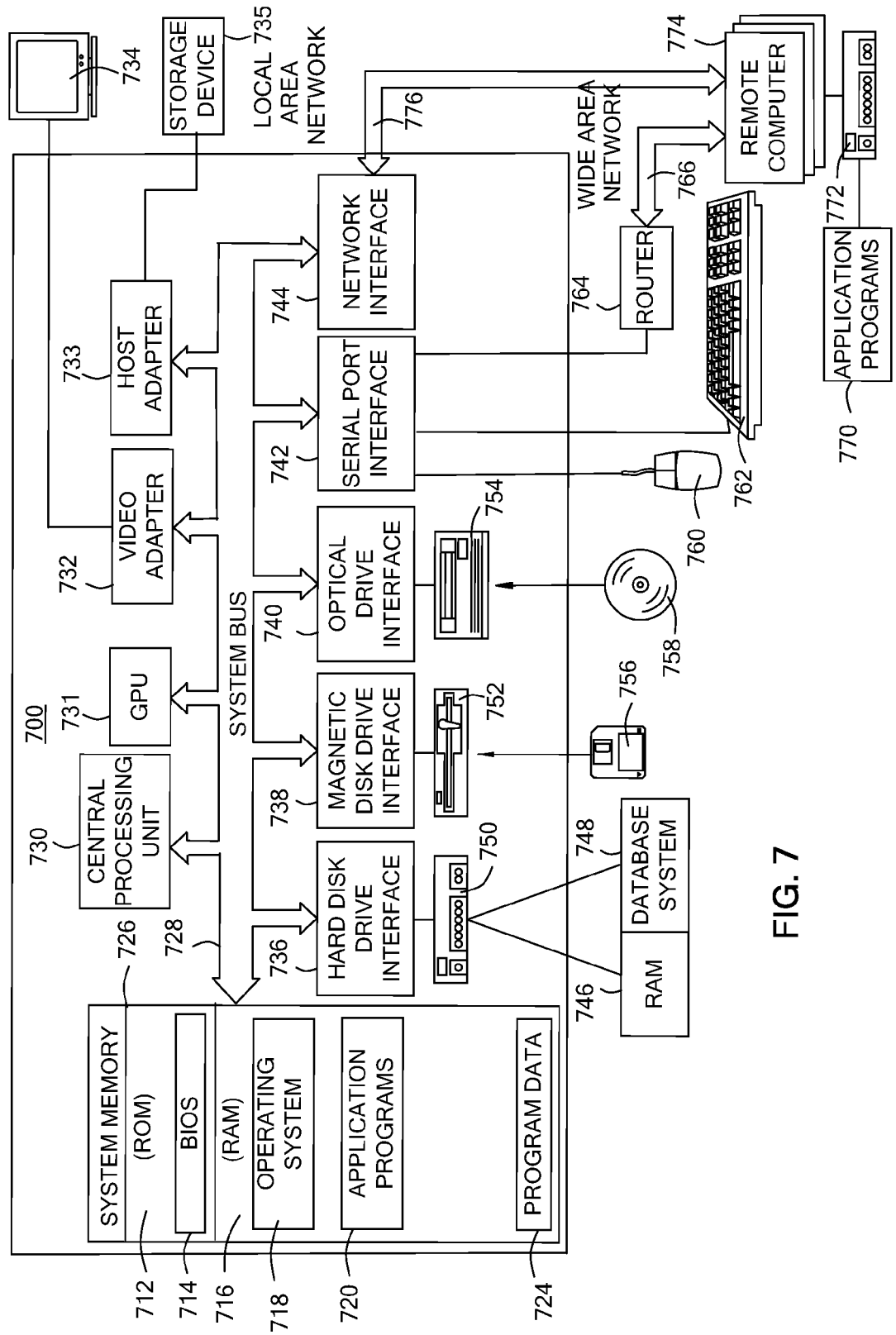
FIG. 7 illustrates a computer system in which the various technologies and techniques described herein may be incorporated and practiced.

FIG. 7 illustrates a schematic diagram of a computing system 700 in which the various technologies described herein may be incorporated and practiced. Although the computing system 700 may be a conventional desktop or a server computer, as described above, other computer system configurations may be used.

The computing system 700 may include a central processing unit (CPU) 730, a system memory 726, a graphics processing unit (GPU) 731 and a system bus 728 that couples various system components including the system memory 726 to the CPU 730. Although one CPU is illustrated in FIG. 7, it should be understood that in some implementations the computing system 700 may include more than one CPU. The GPU 731 may be a microprocessor specifically designed to manipulate and implement computer graphics. The CPU 730 may offload work to the GPU 731. The GPU 731 may have its own graphics memory, and/or may have access to a portion of the system memory 726. As with the CPU 730, the GPU 731 may include one or more processing units, and the processing units may include one or more cores. The system bus 727 may be any of several types of bus structures, including a memory bus or memory controller, a peripheral bus, and a local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus also known as Mezzanine bus. The system memory 726 may include a read-only memory (ROM) 712 and a random access memory (RAM) 716. A basic input/output system (BIOS) 714, containing the basic routines that help transfer information between elements within the computing system 700, such as during start-up, may be stored in the ROM 712.

The computing system 700 may further include a hard disk drive 750 for reading from and writing to a hard disk, a magnetic disk drive 752 for reading from and writing to a removable magnetic disk 756, and an optical disk drive 754 for reading from and writing to a removable optical disk 758, such as a CD ROM or other optical media. The hard disk drive 750, the magnetic disk drive 752, and the optical disk drive 754 may be connected to the system bus 728 by a hard disk drive interface 736, a magnetic disk drive interface 738, and an optical drive interface 740, respectively. The drives and their associated computer-readable media may provide nonvolatile storage of computer-readable instructions, data structures, program modules and other data for the computing system 700.

Although the computing system 700 is described herein as having a hard disk, a removable magnetic disk 756 and a removable optical disk 758, it should be appreciated by those skilled in the art that the computing system 700 may also include other types of computer-readable media that may be accessed by a computer. For example, such computer-readable media may include computer storage media and communication media. Computer storage media may include volatile and non-volatile, and removable and non-removable media implemented in any method or technology for storage of information, such as computer-readable instructions, data structures, program modules or other data. Computer storage media may further include RAM, ROM, erasable programmable read-only memory (EPROM), electrically erasable programmable read-only memory (EEPROM), flash memory or other solid state memory technology, CD-ROM, digital versatile disks (DVD), or other optical storage, magnetic cassettes, magnetic tape, magnetic disk storage or other magnetic storage devices, or any other medium which can be used to store the desired information and which can be accessed by the computing system 700. Communication media may embody computer readable instructions, data structures, program modules or other data in a modulated data signal, such as a carrier wave or other transport mechanism and may include any information delivery media. The term "modulated data signal" may mean a signal that has one or more of its characteristics set or changed in such a manner as to encode information in the signal. By way of example, and not limitation, communication media may include wired media such as a wired network or direct-wired connection, and wireless media such as acoustic, RF, infrared and other wireless media. The computing system 700 may also include a host adapter 733 that connects to a storage device 735 via a small computer system interface (SCSI) bus, a Fiber Channel bus, an eSATA bus, or using any other applicable computer bus interface. Combinations of any of the above may also be included within the scope of computer readable media.

A number of program modules may be stored on the hard disk 750, magnetic disk 756, optical disk 758, ROM 712 or RAM 716, including an operating system 718, one or more application programs 720, program data 724, and a database system 748. The application programs 720 may include various mobile applications ("apps") and other applications configured to perform various methods and techniques described herein. The operating system 718 may be any suitable operating system that may control the operation of a networked personal or server computer, such as Windows® XP, Mac OS® X, Unix-variants (e.g., Linux® and BSD®), and the like.

A user may enter commands and information into the computing system 700 through input devices such as a keyboard 762 and pointing device 760. Other input devices may include a microphone, joystick, game pad, satellite dish, scanner, or the like. These and other input devices may be connected to the CPU 730 through a serial port interface 742 coupled to system bus 728, but may be connected by other interfaces, such as a parallel port, game port or a universal serial bus (USB). A monitor 738 or other type of display device may also be connected to system bus 728 via an interface, such as a video adapter 732. In addition to the monitor 738, the computing system 700 may further include other peripheral output devices such as speakers and printers.

Further, the computing system 700 may operate in a networked environment using logical connections to one or more remote computers 778. The logical connections may be any connection that is commonplace in offices, enterprise-wide computer networks, intranets, and the Internet, such as local area network (LAN) 776 and a wide area network (WAN) 766. The remote computers 774 may be another a computer, a server computer, a router, a network PC, a peer device or other common network node, and may include many of the elements describes above relative to the computing system 700. The remote computers 774 may also each include application programs 770 similar to that of the computer action function.

When using a LAN networking environment, the computing system 700 may be connected to the local network 776 through a network interface or adapter 744. When used in a WAN networking environment, the computing system 700 may include a router 764, wireless router or other means for establishing communication over a wide area network 766, such as the Internet. The router 764, which may be internal or external, may be connected to the system bus 728 via the serial port interface 742. In a networked environment, program modules depicted relative to the computing system 700, or portions thereof, may be stored in a remote memory storage device 735. It will be appreciated that the network connections shown are merely examples and other means of establishing a communications link between the computers may be used.

The network interface 744 may also utilize remote access technologies (e.g., Remote Access Service (RAS), Virtual Private Networking (VPN), Secure Socket Layer (SSL), Layer 2 Tunneling (L2T), or any other suitable protocol). These remote access technologies may be implemented in connection with the remote computers 774.

It should be understood that the various technologies described herein may be implemented in connection with hardware, software or a combination of both. Thus, various technologies, or certain aspects or portions thereof, may take the form of program code (i.e., instructions) embodied in tangible media, such as floppy diskettes, CD-ROMs, hard drives, or any other machine-readable storage medium wherein, when the program code is loaded into and executed by a machine, such as a computer, the machine becomes an apparatus for practicing the various technologies. In the case of program code execution on programmable computers, the computing device may include a processor, a storage medium readable by the processor (including volatile and non-volatile memory and/or storage elements), at least one input device, and at least one output device. One or more programs that may implement or utilize the various technologies described herein may use an application programming interface (API), reusable controls, and the like. Such programs may be implemented in a high level procedural or object oriented programming language to communicate with a computer system. However, the program(s) may be implemented in assembly or machine language, if desired. In any case, the language may be a compiled or interpreted language, and combined with hardware implementations. Also, the program code may execute entirely on a user's computing device, partly on the user's computing device, as a stand-alone software package, partly on the user's computer and partly on a remote computer or entirely on the remote computer or a server computer.

Those with skill in the art will appreciate that any of the listed architectures, features or standards discussed above with respect to the example computing system 700 may be omitted for use with a computing system used in accordance with the various embodiments disclosed herein because technology and standards continue to evolve over time.

Although the subject matter has been described in language specific to structural features and/or methodological acts, it is to be understood that the subject matter defined in the appended claims is not limited to the specific features or acts described above. Rather, the specific features and acts described above are disclosed as example forms of implementing the claims.

While the foregoing is directed to implementations of various technologies described herein, other and further implementations may be devised without departing from the basic scope thereof, which may be determined by the claims that follow. Although the subject matter has been described in language specific to structural features and/or methodological acts, it is to be understood that the subject matter defined in the appended claims is not limited to the specific features or acts described above. Rather, the specific features and acts described above are disclosed as example forms of implementing the claims.

What is claimed is:

1. A method for estimating porosity or permeability in a region of interest, comprising:
   receiving a plurality of chemical measurements for the region of interest, wherein the chemical measurements comprise an amount of silicon, aluminum, potassium and iron in the region of interest;
   determining an amount of biogenic silica in the region of interest using the chemical measurements;
   determining grain density of the region of interest based at least in part on the amount of biogenic silica; and
   determining the porosity or permeability of the region of interest based at least in part on the determined grain density.

2. The method of claim 1, wherein the region of interest comprises one or more predetermined depths in a wellbore.

3. The method of claim 1, wherein the region of interest comprises a plurality of locations in a shale.

4. The method of claim 1, wherein determining the amount of biogenic silica comprises:

determining a first ratio between the amount of silicon in the region of interest and a sum of the amounts of aluminum, potassium, and silicon in the region of interest; and determining a second ratio between the amount of iron in the region of interest and a sum of the amounts of iron and silicon in the region of interest.

5. The method of claim 4, wherein determining the amount of biogenic silica comprises generating a plot of the first ratio with the second ratio.

6. The method of claim 5, wherein the plot comprises the first ratio plotted on the y-axis of the plot and the second ratio is plotted on the x-axis of the plot.

7. The method of claim 5, further comprising determining a threshold line on the plot that represents an approximate minimum amount of biogenic silica in the region of interest.

8. The method of claim 5, further comprising determining a threshold line on the plot that represents an approximate maximum amount of biogenic silica in the region of interest.

9. The method of claim 5, wherein the plot comprises Cartesian coordinates.

10. The method of claim 1, further comprising generating a stimulation plan using the determined porosity or permeability, the stimulation plan having a fluid viscosity of a fracturing fluid or a rate of injection of a fracturing fluid.

11. The method of claim 1, further comprising determining the presence of hydrocarbon deposits in the region of interest using the determined porosity or determined permeability.

12. A non-transitory computer-readable medium having stored thereon computer-executable instructions which, when executed by a computer, cause the computer to:

receive a plurality of chemical measurements for a region of interest, wherein the chemical measurements comprise an amount of silicon, aluminum, potassium and iron in the region of interest;

determine an amount of biogenic silica in the region of interest using the chemical measurements;

determine grain density of the region of interest based at least in part on the amount of biogenic silica; and determine porosity or permeability of the region of interest based at least in part on the determined grain density.

13. The non-transitory computer-readable medium of claim 12, wherein the computer-executable instructions which, when executed by the computer, cause the computer to determine the amount of biogenic silica comprises computer-executable instructions which, when executed by the computer, cause the computer to:

determine a first ratio between the amount of silicon in the region of interest and a sum of the amounts of aluminum, potassium, and silicon in the region of interest; and determine a second ratio between the amount of iron in the region of interest and a sum of the amounts of iron and silicon in the region of interest.

14. The non-transitory computer-readable medium of claim 13, wherein the computer-executable instructions which, when executed by the computer, cause the computer to determine the amount of biogenic silica comprises computer-executable instructions which, when executed by the computer, cause the computer to generate a plot of the first ratio with the second ratio.

15. The non-transitory computer-readable medium of claim 14, wherein the plot comprises the first ratio plotted on the y-axis of the plot and the second ratio is plotted on the x-axis of the plot.

16. The non-transitory computer-readable medium of claim 14, wherein the computer-executable instructions further comprise computer-executable instructions which, when executed by the computer, cause the computer to determine a threshold line on the plot that represents an approximate minimum amount of biogenic silica in the region of interest.

17. The non-transitory computer-readable medium of claim 14, wherein the computer-executable instructions further comprise computer-executable instructions which, when executed by the computer, cause the computer to determine a threshold line on the plot that represents an approximate maximum amount of biogenic silica in the region of interest.

18. The non-transitory computer-readable medium of claim 12, wherein the computer-executable instructions further comprise computer-executable instructions which, when executed by the computer, cause the computer to generate a stimulation plan using the determined porosity or permeability, the stimulation plan having a fluid viscosity of a fracturing fluid or a rate of injection of a fracturing fluid.

19. The non-transitory computer-readable medium of claim 12, wherein the computer-executable instructions further comprise computer-executable instructions which, when executed by the computer, cause the computer to determine the presence of hydrocarbon deposits in the region of interest using the determined porosity or determined permeability.

20. A computer system, comprising:

a computer processor; and a memory comprising program instructions executable by the computer processor to:

receive a plurality of chemical measurements for a region of interest, wherein the chemical measurements comprise an amount of silicon, aluminum, potassium and iron in the region of interest;

determine an amount of biogenic silica in the region of interest using the chemical measurements;

determine grain density of the region of interest based at least in part on the amount of biogenic silica; and determine porosity or permeability of the region of interest based at least in part on the determined grain density.

* * * * *